(12) United States Patent
Madan et al.

(10) Patent No.: US 6,491,708 B2
(45) Date of Patent: Dec. 10, 2002

(54) ULTRASONIC TRANSDUCER WITH IMPROVED COMPRESSIVE LOADING

(75) Inventors: Ashvani K. Madan, Mason, OH (US); Jean M. Beaupre, Blue Ash, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/740,214

(22) Filed: Dec. 19, 2000

(65) Prior Publication Data

US 2001/0001123 A1 May 10, 2001

Related U.S. Application Data

(63) Continuation of application No. 09/292,441, filed on Apr. 15, 1999.

(51) Int. Cl.[7] .............................................. A61B 17/32
(52) U.S. Cl. ........................................ 606/169; 310/334
(58) Field of Search ............................... 606/165–171; 604/22; 601/2; 310/334

(56) References Cited

U.S. PATENT DOCUMENTS

| | | |
|---|---|---|
| 3,636,943 A | 1/1972 | Balamuth |
| 4,438,509 A | 3/1984 | Butler et al. |
| 5,322,055 A | 6/1994 | Davison et al. |
| 5,324,299 A | 6/1994 | Davison et al. |
| 5,425,704 A * | 6/1995 | Sakuai et al. ................ 606/169 |
| 5,746,756 A | 5/1998 | Bromfield et al. |
| 5,798,599 A | 8/1998 | Harwood |
| 5,836,897 A * | 11/1998 | Sakurai et al. ............... 606/169 |
| 5,989,275 A * | 11/1999 | Estabrook et al. ........... 606/169 |

FOREIGN PATENT DOCUMENTS

GB 868784 5/1961

\* cited by examiner

*Primary Examiner*—Peter Nerbun
*Assistant Examiner*—Katherine Moran
(74) *Attorney, Agent, or Firm*—Verne E. Kreger

(57) ABSTRACT

An ultrasonic device with increased efficiency as a result of substantially increased pressure uniformity across individual PZTs and through the PZT stack. Specifically, the PZT stack is uniformly compressed by way of a bolt having a head that has a surface area roughly equal to the surface area of the individual piezoelectric elements. The bolt is further combined with an aft end bell that has a reduced surface contact with the bolt head and a larger surface contact with the adjacent piezoelectric stack.

12 Claims, 11 Drawing Sheets

ULTRASONIC TRANSDUCER WITH IMPROVED COMPRESSIVE LOADING

This application is a continuation of application Ser. No. 09/292,441, filed Apr. 15, 1999.

BACKGROUND OF THE INVENTION

The present invention relates generally to ultrasonic transducer assemblies and, in particular to transducer assemblies of the composite or sandwich type with a compression assembly for providing a more uniformly compressive loading to the transducer assembly.

Ultrasonic transmission devices are well known for use in a variety of applications, such as surgical operations and procedures. The ultrasonic transmission devices usually include a transducer that converts electrical energy into vibrational motion at ultrasonic frequencies. The vibrational motion is transmitted to vibrate a distal end of a surgical instrument. Such uses are disclosed in representative U.S. Pat. Nos. 3,636,943 and 5,746,756, both incorporated herein by reference.

High-intensity ultrasonic transducers of the composite or sandwich type typically include front and rear mass members with alternating annular piezoelectric transducers and electrodes stacked therebetween. Most such high-intensity transducer are of the pre-stressed type. They employ a compression bolt that that extends axially through the stack to place a static bias of about one-half of the compressive force that the piezoelectric (PZT) transducers can tolerate. Sandwich transducers utilizing a bolted stack transducer tuned to a resonant frequency and designed to a half wavelength of the resonant frequency are described in United Kingdom Patent No. 868,784. When the transducers operate they are designed to always remain in compression, swinging from a minimum compression of nominally zero to a maximum peak of no greater than the maximum compression strength of the material.

As shown in FIG. 1, an acoustic or transmission assembly 80 of an ultrasonic device generally includes a transducer stack or assembly 82 and a transmission component or working member. The transmission component may include a mounting device 84, a transmission rod or waveguide 86, and an end effector or applicator 88. The transmission rod 86 and end effector 88 are preferably part of a surgical instrument.

The transducer assembly 82 of the acoustic assembly 80 converts the electrical signal from a generator (not shown) into mechanical energy that results in longitudinal vibratory motion of the end effector 88 at ultrasonic frequencies. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. The transducer assembly 82, which is known as a "Langevin stack", generally includes a transduction portion 90, a first resonator or aft end bell 92, and a second resonator or fore end bell 94. The transducer assembly 82 is preferably an integral number of one-half system wavelengths (nλ/2) in length.

The distal end of the first resonator 92 is connected to the proximal end of transduction section 90, and the proximal end of the second resonator 94 is connected to the distal end of transduction portion 90. The first and second resonators 92 and 94 are preferably fabricated from titanium, aluminum, steel, or any other suitable material. The first and second resonators 92 and 94 have a length determined by a number of variables, including the thickness of the transduction section 90, the density and modulus of elasticity of material used in the resonators 92 and 94, and the fundamental frequency of the transducer assembly 82. The second resonator 94 may be tapered inwardly from its proximal end to its distal end to amplify the ultrasonic vibration amplitude.

The transduction portion 90 of the transducer assembly 82 preferably comprises a piezoelectric section ("PZTs") of alternating positive electrodes 96 and negative electrodes 98, with piezoelectric elements 100 alternating between the electrodes 96 and 98. The piezoelectric elements 100 may be fabricated from any suitable material, such as, for example, lead zirconate-titanate, lead meta-niobate, lead titanate, or ceramic piezoelectric crystal material. Each of the positive electrodes 96, negative electrodes 98, and piezoelectric elements 100 have a bore extending through the center. The positive and negative electrodes 96 and 98 are electrically coupled to wires 102 and 104, respectfully. The wires 102 and 104 transmit the electrical signal from the generator to electrodes 96 and 98.

The piezoelectric elements 100 are energized in response to the electrical signal supplied from the generator to produce an acoustic standing wave in the acoustic assembly 80. The electrical signal causes disturbances in the piezoelectric elements 100 in the form of repeated small displacements resulting in large compression forces within the material. The repeated small displacements cause the piezoelectric elements 100 to expand and contract in a continuous manner along the axis of the voltage gradient, producing high frequency longitudinal waves of ultrasonic energy. The ultrasonic energy is transmitted through the acoustic assembly 80 to the end effector 88.

The piezoelectric elements 100 are conventionally held in compression between the first and second resonators 92 and 94 by a bolt and washer combination 106. The bolt 106 preferably has a head, a shank, and a threaded distal end. The bolt 106 is inserted from the proximal end of the first resonator 92 through the bores of the first resonator 92, the electrodes 96 and 98, and piezoelectric elements 100. The threaded distal end of the bolt 106 is screwed into a threaded bore in the proximal end of second resonator 94.

Other embodiments of the prior art utilize a stud that is threadedly engaged with both the first and second resonators 92 and 94 to provide compressive forces to the PZT stack. Threaded studs are also known in the prior art for attaching and detaching transmission components to the transducer assembly. See, for example, U.S. Pat. Nos. 5,324,299 and 5,746,756. Such bolts and studs are utilized to maintain acoustic coupling between elements of the sandwich type transducer or any attached acoustic assembly. Coupling is important to maintain tuning of the assembly, allowing the assembly to be driven in resonance.

The problem with the prior art is that the compression means is inadequate and is unable to provide a uniform pressure across the inside diameter to the outside diameter of each PZT and through the entire PZT stack, the "r" and "z" axes as shown in FIG. 1 and graphically illustrated in FIG. 2. A Finite Element analysis shows that the ratio of the pressure in the r axis is of the order of 4:1.

Non-uniform pressure across the r and z axes reduces transducer efficiency and leads to high heat generation. This limitation becomes acutely critical in temperature-limited applications. In temperature-limited applications, the reduced efficiency translates into higher heat generation in the transducer and reduced maximum output. Further, non-uniform pressure limits the magnitude of compression and therefore limits the power capability of the transducer.

U.S. Pat. No. 5,798,599 discloses an ultrasonic transducer assembly which includes soft, aluminum foil washers disposed between facing surfaces of adjacent members of the PZT stack. The washers deform under compressive loading to follow the surface irregularities of the adjacent member surfaces.

There is a need therefore, for an ultrasonic transducer that exhibits substantially uniform compressive stresses across each PZT and throughout the PZT stack to reduce heat generation and increase power output efficiency. This invention meets this need.

SUMMARY OF THE INVENTION

The invention is an ultrasonic device with increased efficiency as a result of substantially increased pressure uniformity across individual PZTs and through the PZT stack. The invention comprises a transducer assembly adapted to vibrate at an ultrasonic frequency in response to electrical energy, the transducer assembly comprising; a stack of alternating positive and negative electrodes and piezoelectric elements in an alternating relationship with the electrodes; a mounting device having a first end and a second end, the mounting device adapted to receive ultrasonic vibration from the stack and to transmit the ultrasonic vibration from the first end to the second end of the mounting device; and structural means for applying compression forces to the stack, the stack being held together solely by said compression means, and the compression means comprises a surface for applying compression forces, the surface having a surface area substantially equivalent to the surface area of an individual piezoelectric element.

In a further embodiment the compression means comprises a spacer element disposed between the surface area and the piezoelectric elements. The spacer element is configured to comprise a first and second contact area wherein the first contact area is in contact with the surface area and has a smaller area than the second contact area, which is in contact with the proximal end of the piezoelectric stack.

In one embodiment, the PZT stack is uniformly compressed by way of a threaded bolt that has a bolt head surface area roughly equal to the surface area of the individual piezoelectric elements. The bolt can be further combined with a selectively configured end bell that has a first contact surface in contact with the bolt head and a second contact surface in contact with the adjacent piezoelectric stack. The second contact surface has a greater surface area than the first contact surface.

An advantage of the current invention is that the transducer thermal and power efficiencies increase.

A further advantage of the current invention is that heat generation decreases to a degree that active cooling systems are not necessary.

A still further advantage is that uniform pressure allows larger compression magnitudes which in turn leads to larger actuation magnitude. A larger actuation magnitude results in an increase of the useable range of the PZT.

These and other features and advantages of the present invention will become apparent from the following more detailed description, when taken in conjunction with the accompanying drawings which illustrate, by way of example, the principles of the invention.

It is to be understood that both the foregoing general description and the following detailed description are exemplary and explanatory and are intended to provide further explanation of the invention as claimed.

BRIEF DESCRIPTION OF THE DRAWINGS

FIG. 2 is an exemplary contour plot of the pressure loading across each PZT and through the PZT stack of FIG. 1a;

DESCRIPTION OF THE PREFERRED EMBODIMENTS

Before explaining the present invention in detail, it should be noted that the invention is not limited in its application or use to the details of construction and arrangement of parts illustrated in the accompanying drawings and description. Rather, the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

Figure 1:
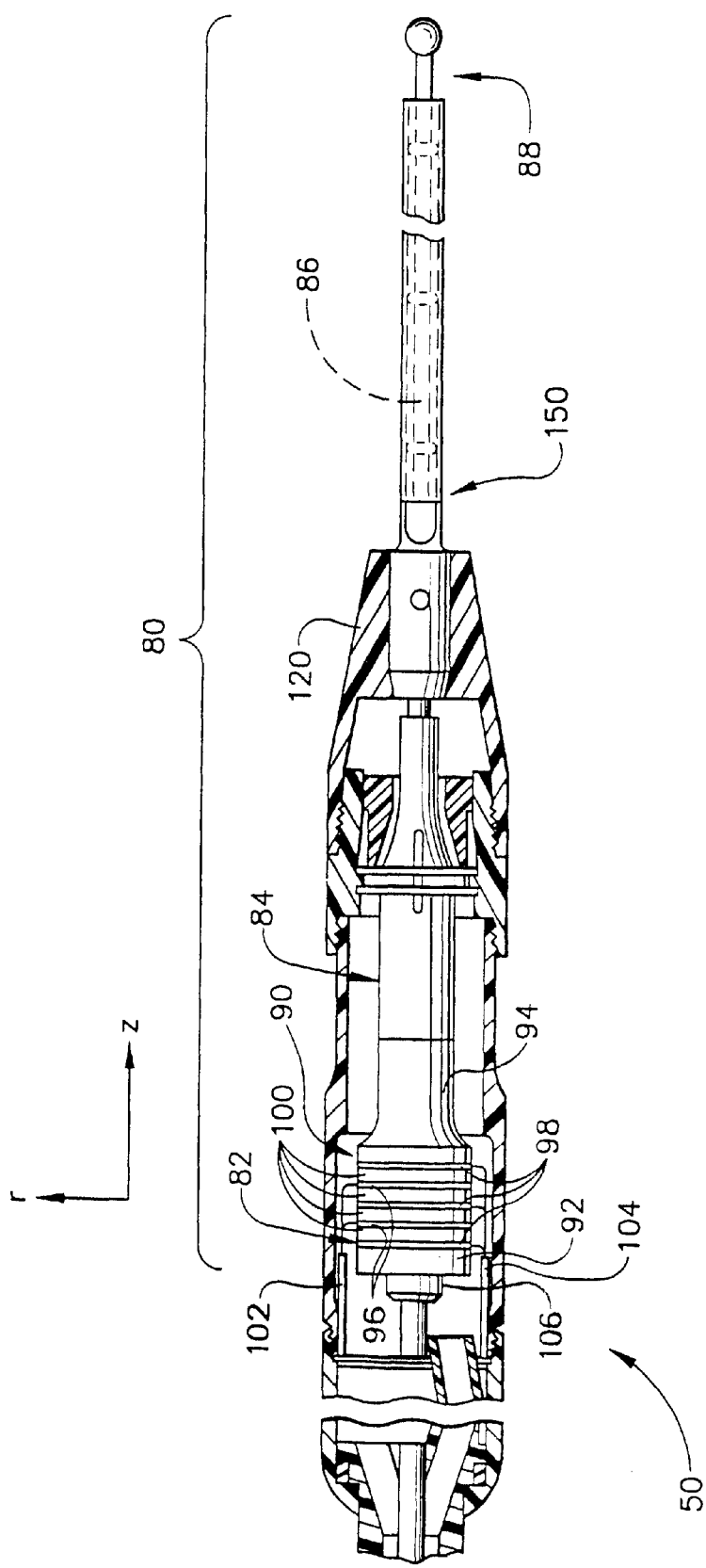
FIG. 1 is a cutaway view and in partial cross-section of an embodiment of a prior art transducer for use in a surgical system.
Figure 2:
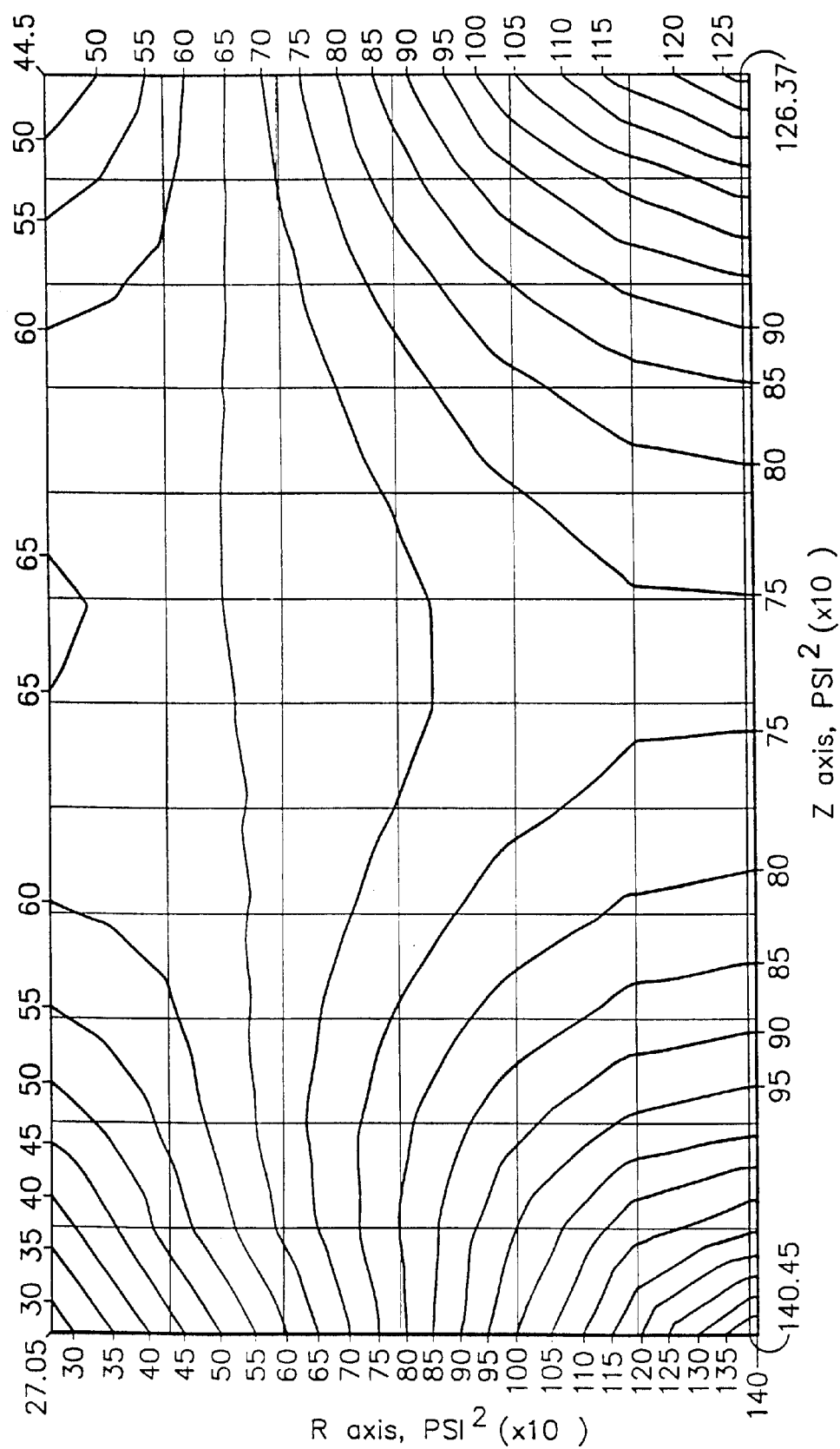
Figure 3:
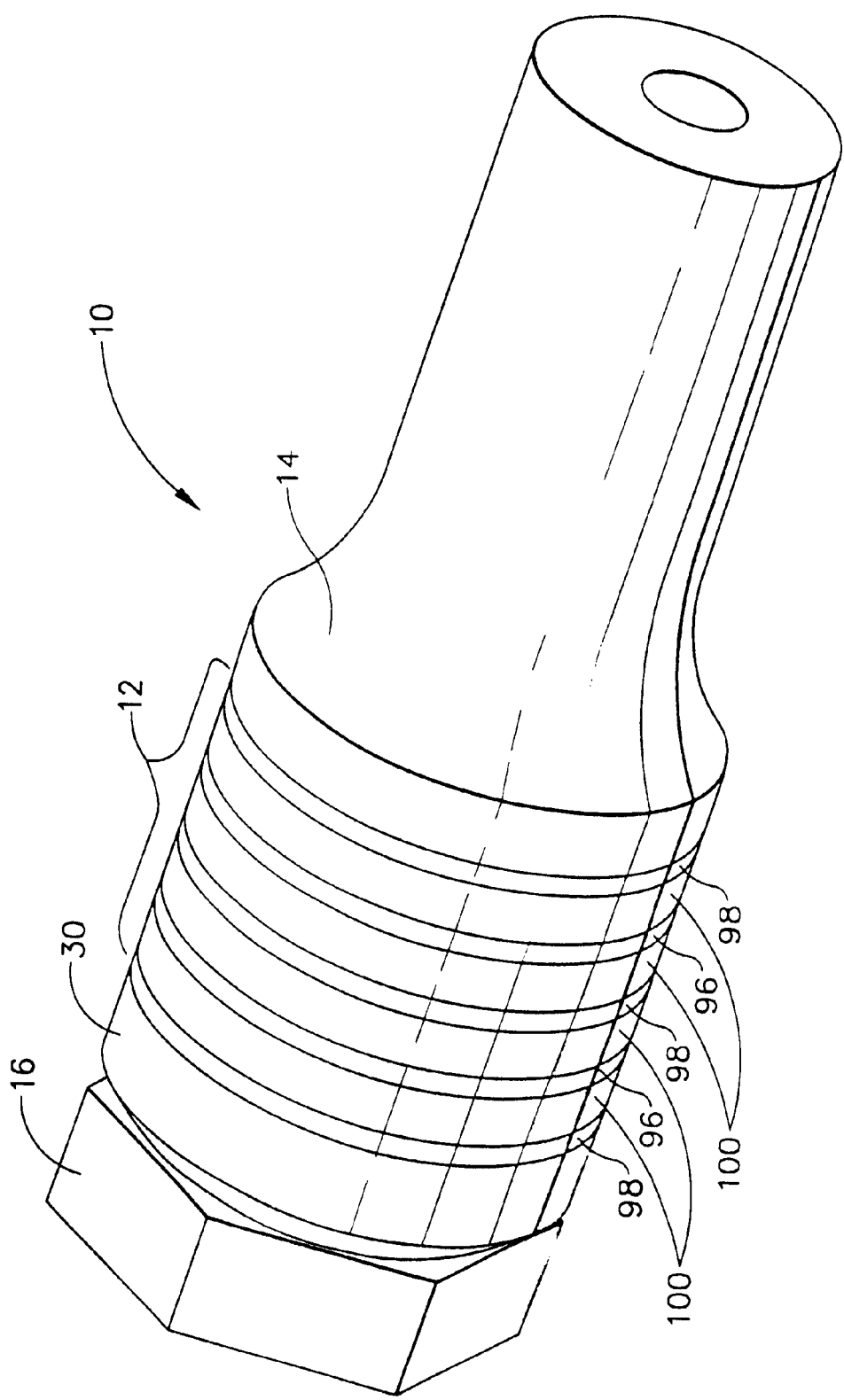
FIG. 3 is a perspective view of a transducer in accordance with the invention.

Referring now to FIG. 3, a transducer assembly 10 of the present invention comprises a PZT stack assembly 12 in combination with a fore end bell 14. The PZT stack is held in compression by a bolt 16 preferably in combination with a specially configured aft end bell 30. Preferably, bolt 16 threadedly engages the fore end bell 14 as discussed above.

Figure 4:
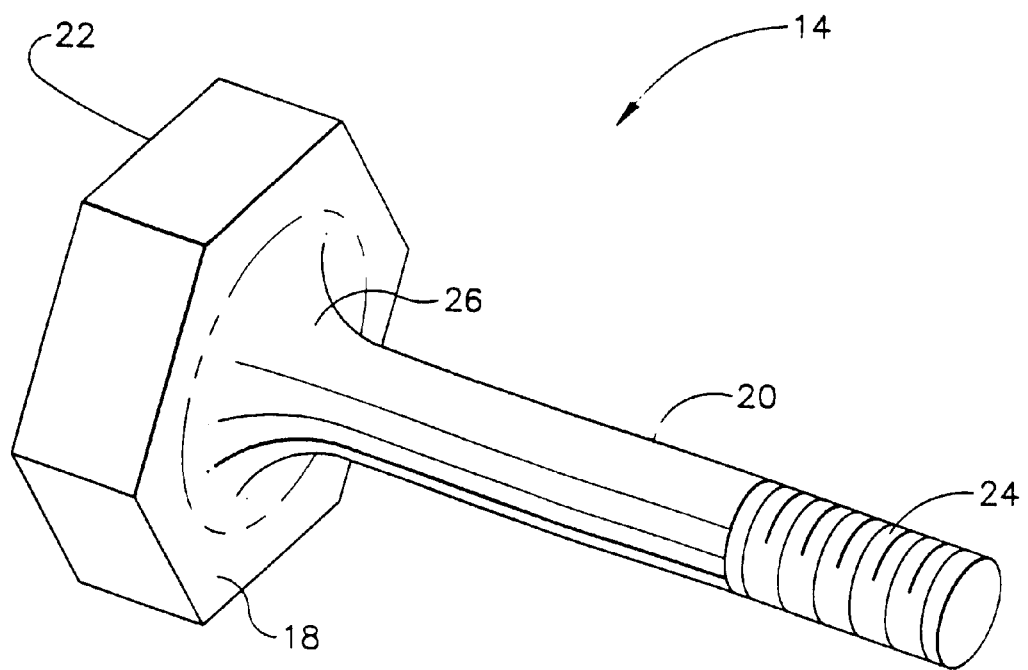
FIG. 4 is a perspective view of the bolt in accordance with the invention.
Figure 5B:
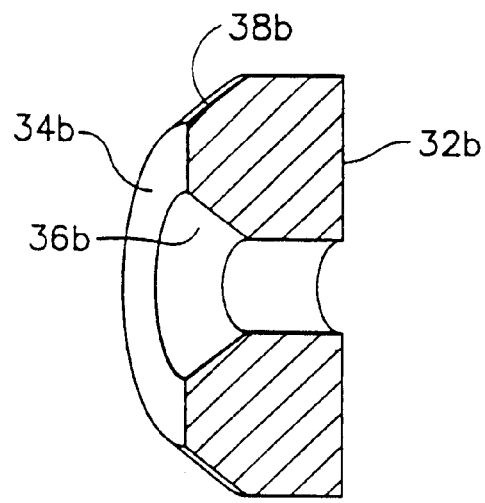
FIGS. 5b–g are cross-sectional perspective views of alternate embodiments of the aft end bell in accordance with the invention.
Figure 5C:
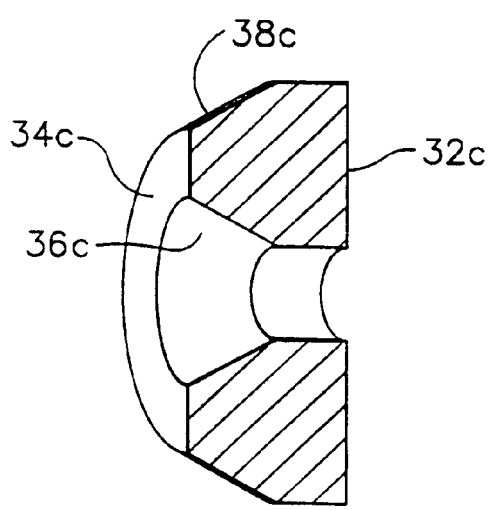
Figure 5D:
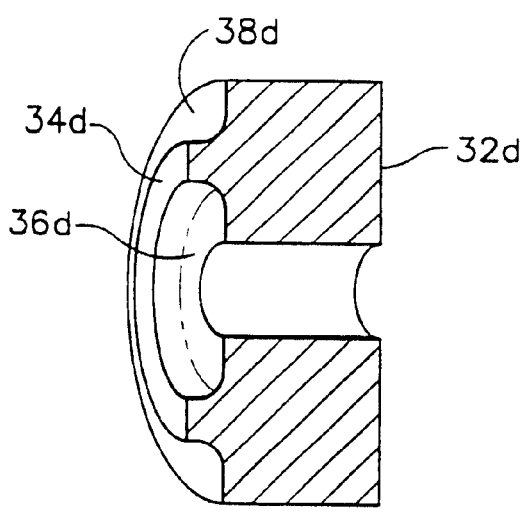
Figure 5E:
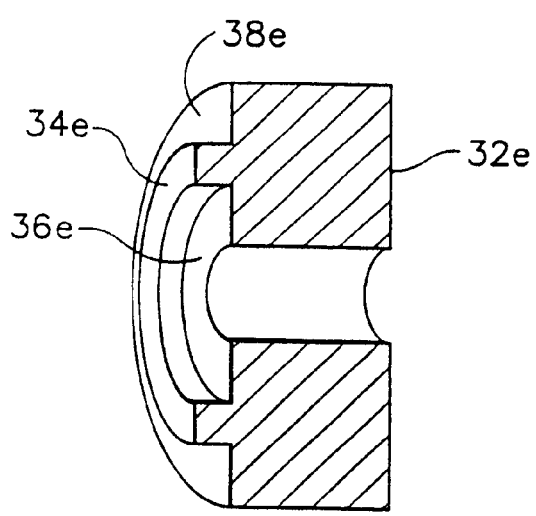
Figure 5F:
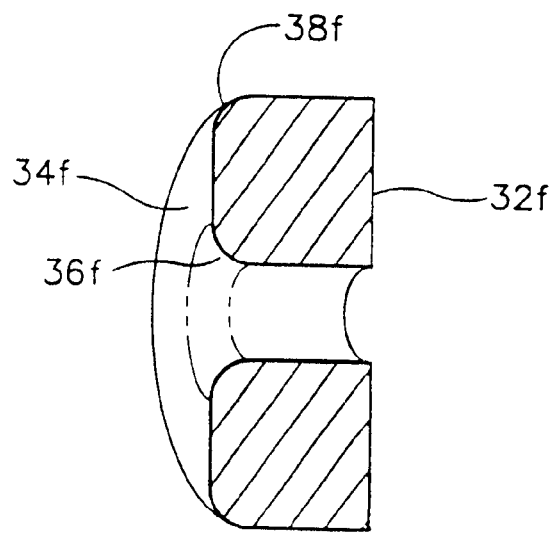
Figure 5G:
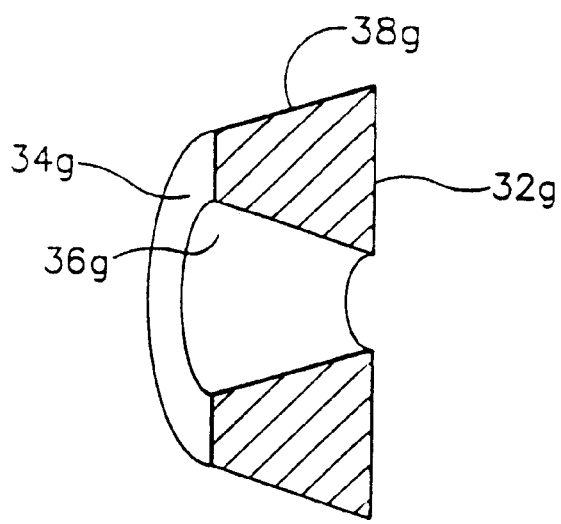

FIG. 4 illustrates bolt 16, which consists of a shank 20 and head 22. Shank 20 is threaded at its distal end 24 to engage a threaded portion (not shown) within the fore end bell 14. Shank 20 flares out at its proximal end 26 where shank 20 meets head 22 to reduce stress concentrations, increase fatigue life and reduce viscoelastic damping. The geometry of the proximal end 26 is only limited by the design constraints of the associated PZT stack and the overall transducer assembly 10. The diameter of bolt head 22 is substantially equal to the diameters of the individual PZTs. Preferably, bolt 16 is made from titanium. Utilizing bolt 16 alone to compressively load PZT stack 12, it was observed that the pressure distribution across each PZT and through the PZT stack substantially improved over the prior art compression means. Specifically, for an equivalent torque applied to the compression means of the invention and the prior art bolt compression means, an increased output voltage is observed with the invention.

Figure 5A:
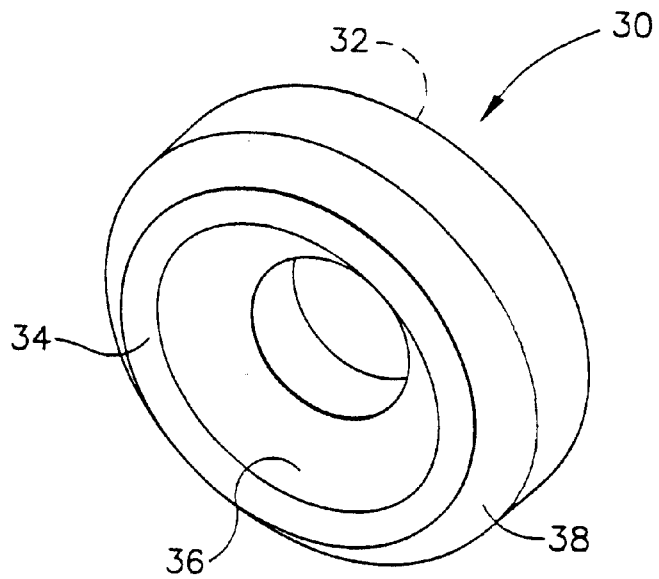
FIG. 5a is a perspective view of the aft end bell in accordance with the invention.

In an alternate embodiment, bolt 16 is combined with aft end bell 30, shown in FIG. 5a. Aft end bell 30 has a first contact surface 32 and a second contact surface 34. The surface area of contact surface 34 is less than the surface area of contact surface 32. Contact surface 34 contacts with surface 18 of bolt 16, and contact surface 32 contacts the first element of PZT stack 12.

An inner chamfer or offset 36 and an outer chamfer or offset 38 define contact surface 34. The specific dimension of contact surface 34 may be optimized through a Finite Element analysis that provides for the greatest uniform pressure across each PZT and through the PZT stack within the given space limitations of the transducer assembly. Optimized or not, so long as the area of contact surface 34 is less than the area of contact surface 32, the pressure loading of the PZT stack will improve over that of the prior art. By compressively loading the contact surface 34, stress concentrations uniformly disperse in the r and z axes and within a short distance of the aft end bell thickness, thereby reducing the necessary aft end bell thickness required to evenly distribute the stress. The inner chamfer 36 also advantageously accommodates the proximal end 26 of shank 20. Preferably, the bevel angle of the inner and outer chamfer 36 and 38 are equal, but it is not required. An exemplary bevel angle is 45°.

Figure 6:
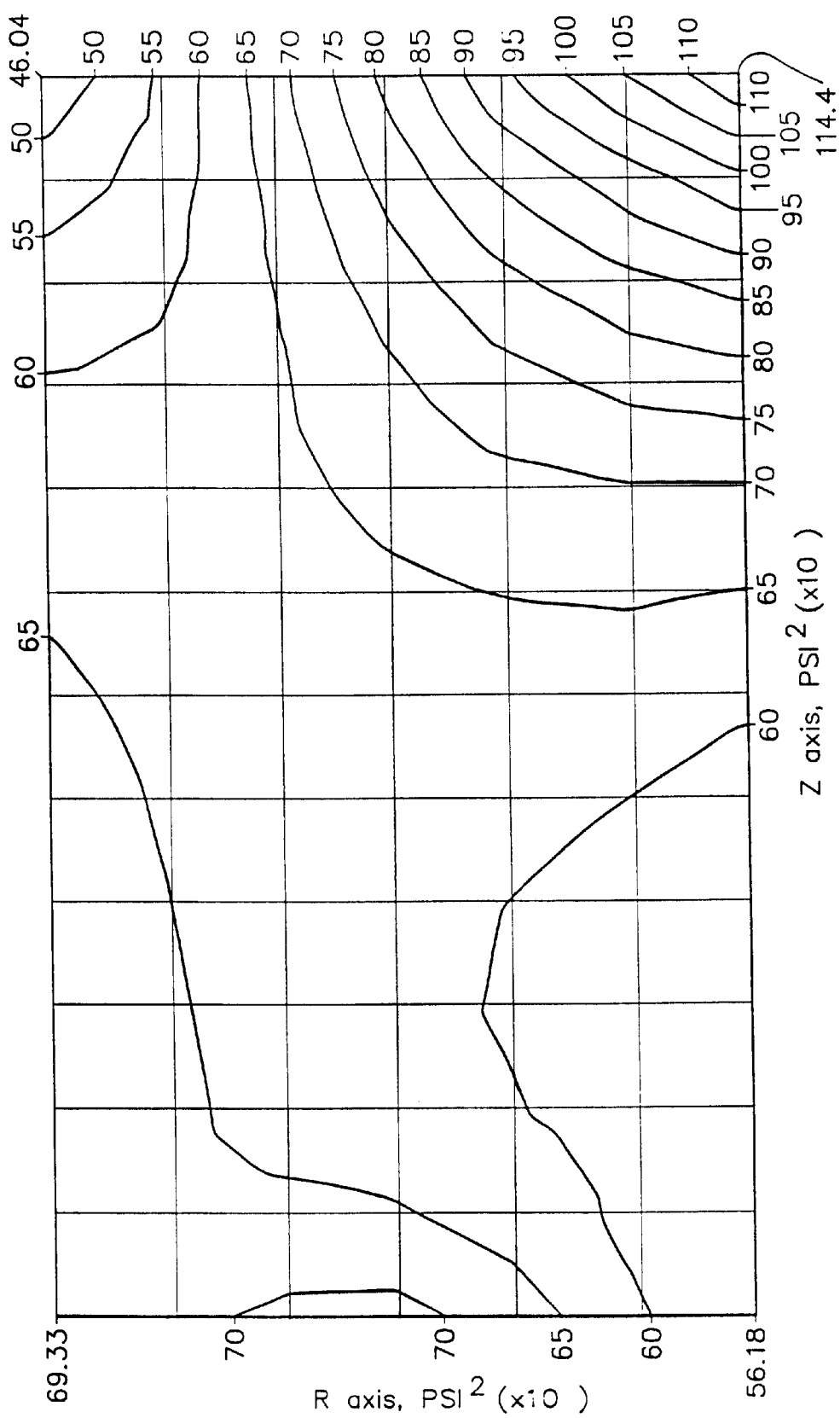
FIG. 6 is an exemplary contour plot of the pressure loading of each PZT and through the PZT stack of a transducer in accordance with the invention.

Utilizing the embodiment of FIG. 3, FIG. 6 illustrates that the ratio of the pressure along the r axis is of the order of 1.3:1. It is also apparent that the compressive forces are more uniform in the z direction at the proximal end of the PZT stack. Further, the invention also reduces the pressure variation in the z direction at the distal end of the PZT stack or at fore end bell surface of the stack as compared with the prior art.

FIGS. 5b–g illustrate alternate embodiments of aft end bell 30. Each embodiment defines a respective contact surface 34b–g smaller in surface area than a respective contact surface 32b–g. A first and second offset 36b–g and 38b–g define each contact surface 34b–g respectively. As is readily apparent, offsets 36b–g and 38b–g can take on any number of varying geometries to define contact surface 34b–g.

Table 1, below, compares the measured transducer efficiency of the present invention with the efficiencies of the prior art.

TABLE I

| PZT Compression Method | Power (W) required for 100 micron Displacement | Efficiency Normalized to the Present Invention (%) |
| --- | --- | --- |
| Bolt with Head | 17.9 | 74 |
| Stud | 16.2 | 81 |
| Present Invention | 13.2 | 100 |

Figure 7:
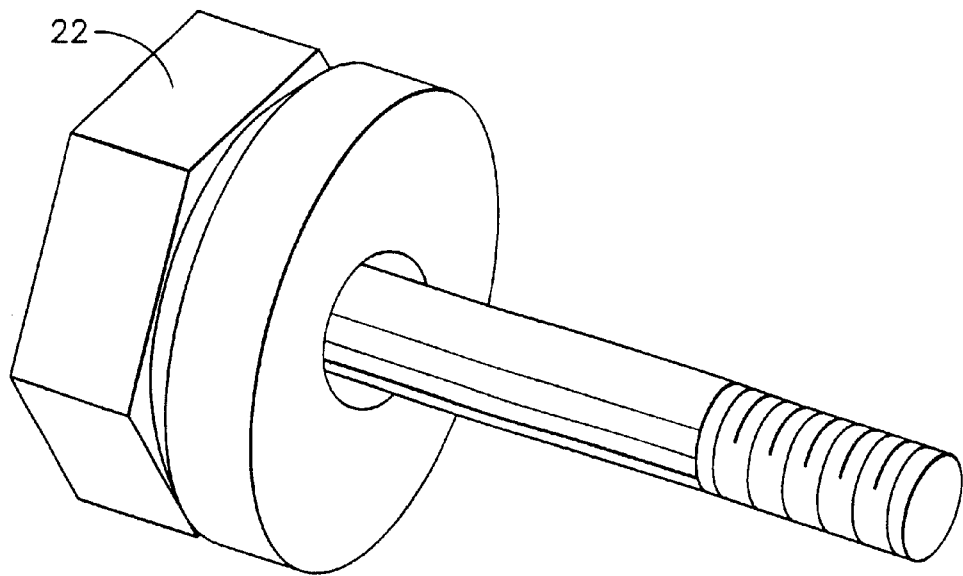
FIG. 7 is a perspective view of an alternate embodiment of the bolt in accordance with the invention.
Figure 8:
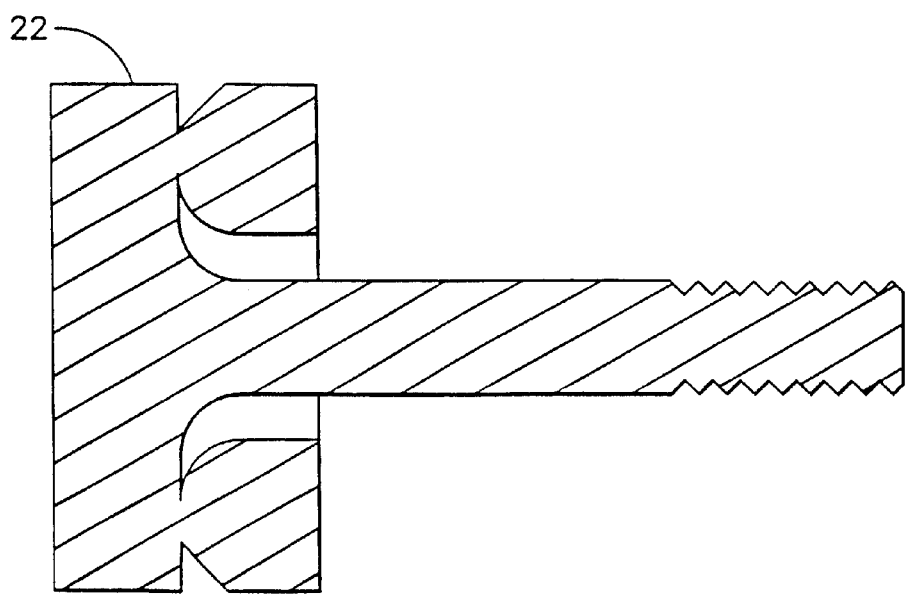
FIG. 8 is a cross-section of the bolt in FIG. 7.

Although the present invention has been described in detail by way of illustration and example, it should be understood that a wide range of changes and modifications could be made to the preferred embodiments described above without departing in any way from the scope and spirit of the invention. For example, FIGS. 7 and 8 illustrate an alternate embodiment of the invention wherein the aft end bell configuration is an integral element of the bolt head 22.

Figure 9:
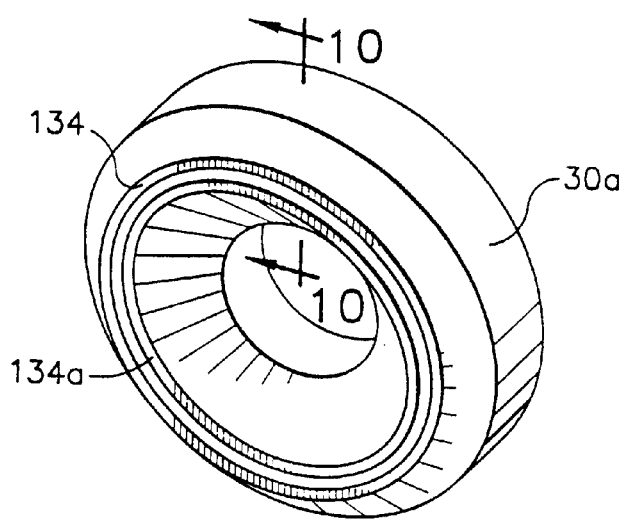
FIG. 9 is a perspective view alternate embodiment of the aft end bell in accordance with the invention.
Figure 10:
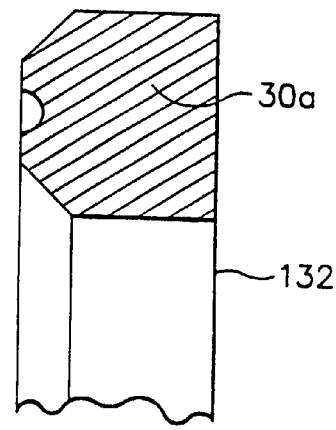
FIG. 10 is an elevation view of the embodiment of FIG. 9.

Multiple aft end bells may be implemented in conjunction with bolt 16. In this embodiment, a first aft end bell 30 is as shown in FIG. 5. A second aft end bell 30a, as shown in FIGS. 9 and 10, may be inserted between end bell 30 and the PZT stack 12. The addition of end bell 30a effectively smoothes out the pressure variations along the r and z axes more so than with the use of end bell 30 alone. End bell 30a comprises two contact surfaces 134 and 134a adjacent to contact surface 32. Contact surface 132 in turn contacts the first piezoelectric element of PZT stack 12. The specific dimensions of contact surfaces 134 and 134a are determined by a Finite Element analysis that provides for the greatest uniform pressure across each PZT and through the PZT stack within the given space limitations of the transducer assembly.

Figure 11:
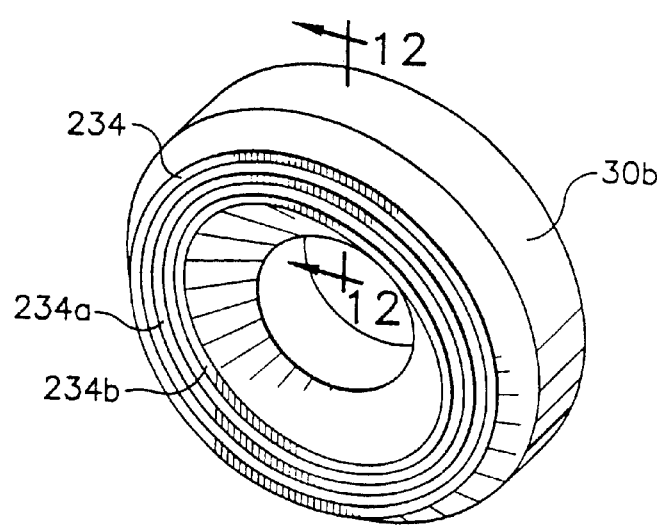
FIG. 11 is a perspective view of another alternate embodiment of the aft end bell in accordance with the invention.
Figure 12:
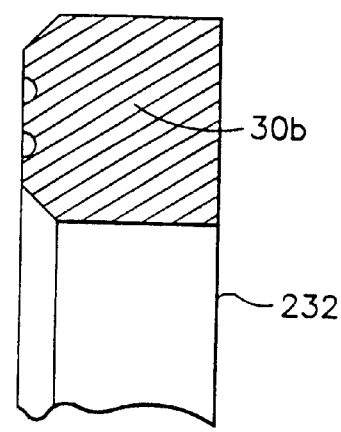
FIG. 12 is an elevation view of the embodiment of FIG. 12.

A third end bell 30b may also be included. The addition of end bell 30b, as shown in FIGS. 11 and 12, between end bell 30a and PZT stack 12 effectively smoothes out the pressure variations along the r and z axes more so than with the use of just end bells 30 and 30a. End bell 30b comprises three contact surfaces 234, 234a and 234b and are adjacent to contact surface 132. Contact surface 232 in turn contacts the first piezoelectric element of PZT stack 12. The specific dimensions of contact surfaces 234, 234a and 234b are determined by a Finite Element analysis that provides for the greatest uniform pressure across each PZT and through the PZT stack within the given space limitations of the transducer assembly. As would be readily apparent to those skilled in the art, additional aft end bells, with a corresponding number of contact surfaces, may be added to further reduce pressure variations within the PZT stack 12.

Figure 13:
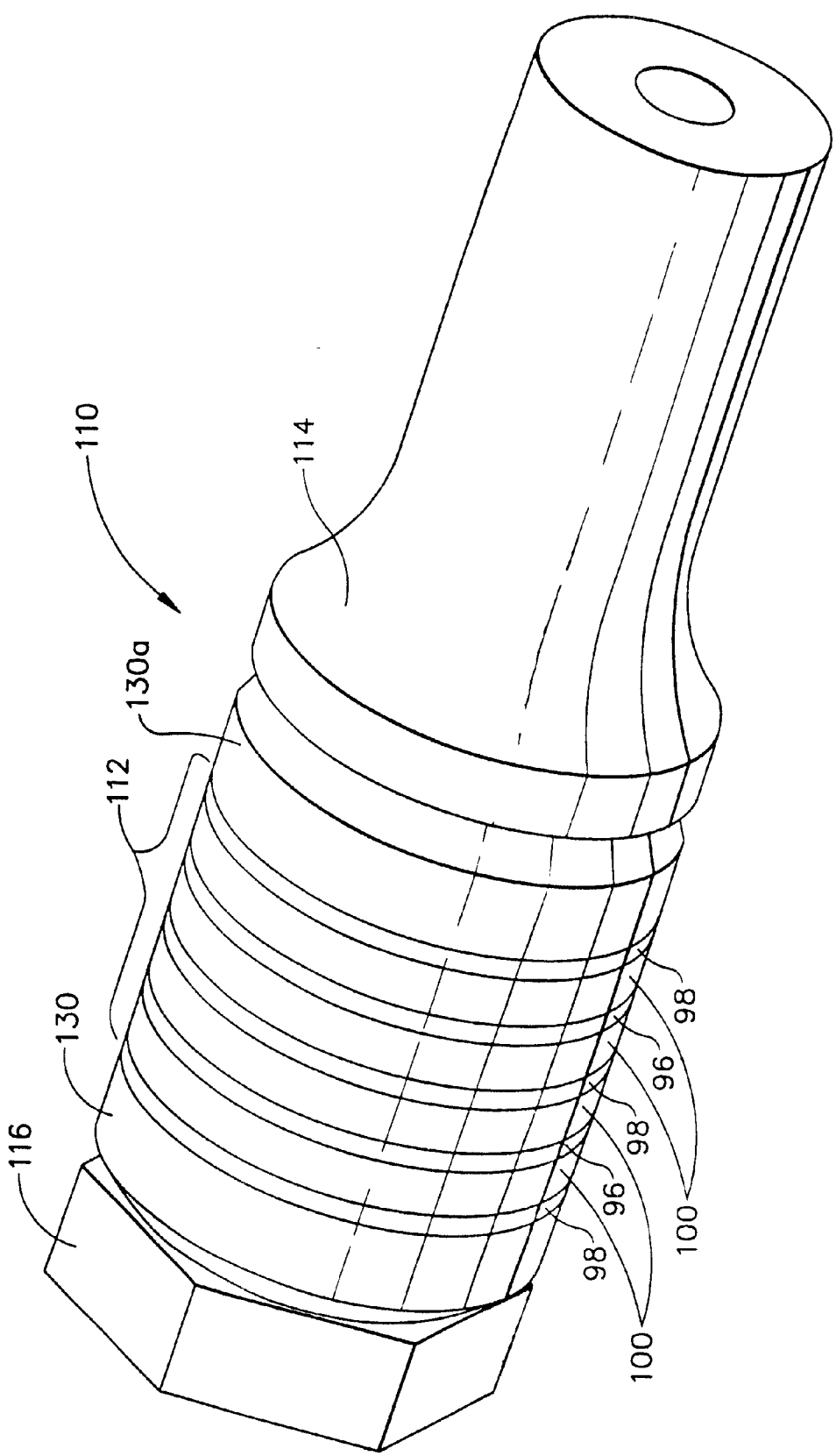
FIG. 13 is a perspective view of an alternate embodiment of the invention with two aft end bells disposed on either end of the PZT stack.

Further, as would be appreciated by one skilled in the art, one or more aft end bells may be incorporated between the PZT stack and fore end bell as shown in FIG. 13. A transducer assembly 110 of the present invention comprises a PZT stack assembly 112 in combination with a fore end bell 114. The PZT stack is held in compression by a bolt 116 in combination with a specially configured aft end bell 130 in accordance with the invention. Bolt 116 threadedly engages the fore end bell 114 as discussed above. Disposed between fore end bell 114 and PZT stack 112 is a second aft end bell 130a in accordance with the invention.

Figure 14:
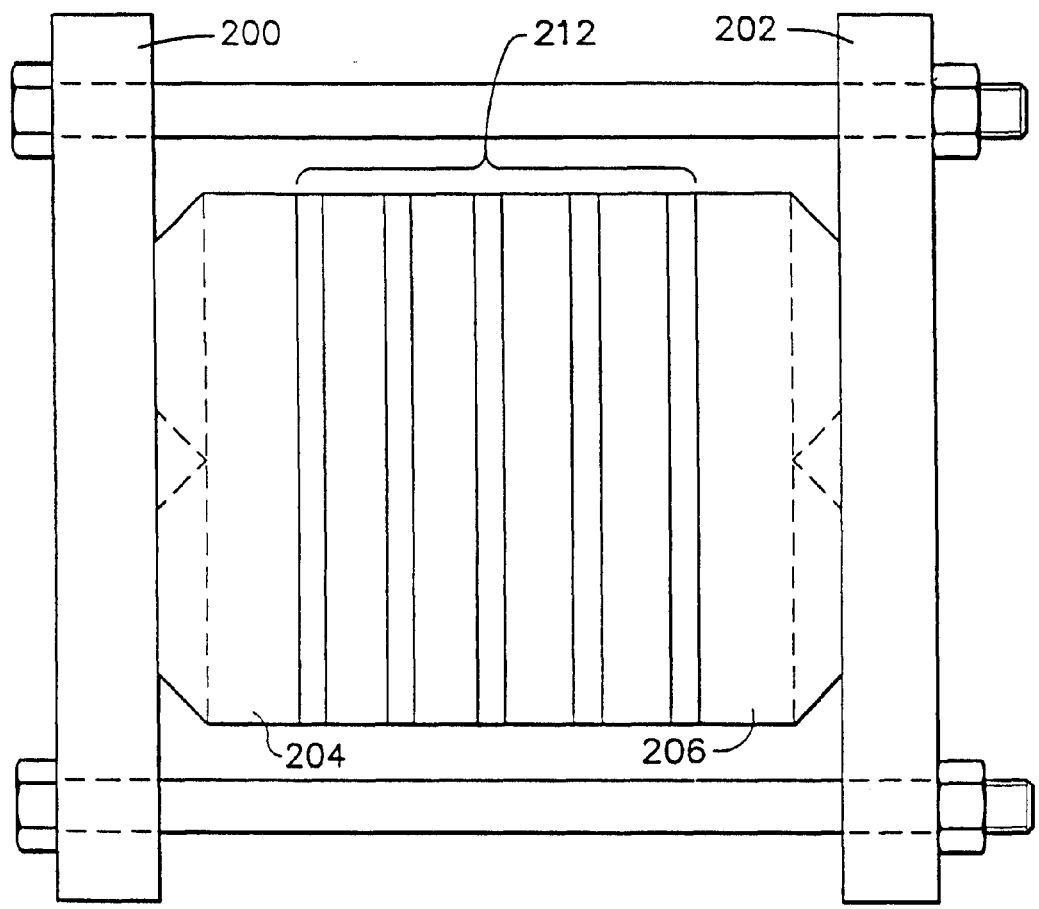
FIG. 14 is a cross-sectional elevation of an alternate means of compressing the PZT stack in accordance with the invention.

Means to hold the PZT stack in compression may include various other embodiments other than a bolt or stud centrally located along the longitudinal axis of the PZT stack. FIG. 14 illustrates an alternate embodiment where the PZT stack 212 is held in compression by way of two end plates 200 and 202 held in place by threaded bolts. In this embodiment, aft end bells 204 and 206, constructed in accordance with the invention, do not have an annular bore since the bore is not required to accept a centrally positioned bolt or stud.

Thus, the described embodiments are to be considered in all aspects only as illustrative and not restrictive, and the scope of the invention is, therefore, indicated by the appended claims rather than the foregoing description. All changes that come within the meaning and range of equivalency of the claims are to be embraced within their scope.

We claim:

1. An ultrasonic device comprising:

a transducer assembly adapted to vibrate at an ultrasonic frequency in response to electrical energy, the transducer assembly comprising;

a stack of alternating positive and negative electrodes and piezoelectric elements in an alternating relationship with the electrodes;

a mounting device having a first end and a second end, the mounting device adapted to receive ultrasonic vibration from the stack and to transmit the ultrasonic vibration from the first end to the second end of the mounting device; and a bolt threadedly engaged with the mounting device comprising a surface substantially equivalent to the surface area of an individual piezoelectric element for applying compression forces to the stack, and an element having a first contact surface adjacent to the stack and a second contact surface adjacent to the bolt surface, wherein the second contact surface area is less than the first contact surface area.

2. The device of claim 1 wherein said element comprises a beveled surface defining the second contact surface.

3. The device of claim 1 wherein said element comprises a first and second beveled surface defining the second contact surface.

4. The device of claim 1 wherein the element is annular in shape.

5. The device of claim 1 wherein the element comprises at least two contact surfaces adjacent to the surface, wherein the surface area of the at least two contact surfaces is less than the first contact surface area.

6. An ultrasonic device comprising:

a transducer assembly adapted to vibrate at an ultrasonic frequency in response to electrical energy, the transducer assembly comprising;

alternating annular positive and negative electrodes and annular piezoelectric elements in alternating relationship with the electrodes to form a stack having a longitudinal axis;

a mounting device having a first end and a second end, the mounting device adapted to receive ultrasonic vibration from the stack and to transmit the ultrasonic vibration from the first end to the second end of the mounting device; and a bolt threadedly engaged with the mounting device along the longitudinal axis for applying compression forces to the stack, the bolt comprising a surface for applying compression forces, the surface having a surface area in an overlapping relationship with the stack; and an element having a first contact surface area adjacent to the stack and a second contact surface area adjacent to the bolt surface, the second contact surface area less than the first contact surface area.

7. The device of claim 6 wherein the element comprises at least two contact surfaces adjacent to the surface, wherein the surface area of the at least two contact surfaces is less than the first contact surface area.

8. The device of claim 6 wherein the element is annular in shape.

9. An ultrasonic surgical device comprising:

a transducer assembly adapted to vibrate at an ultrasonic frequency in response to electrical energy, the transducer assembly comprising:

alternating annular positive and negative electrodes and annular piezoelectric elements in alternating relationship with the electrodes to form a stack having a longitudinal axis;

a mounting device having a first end and a second end, the mounting device adapted to receive ultrasonic vibration from the stack and to transmit the ultrasonic vibration form the first end to the second end of the mounting device; and a first compression means for applying compression forces to the stack, and the compression means comprises a surface for applying compression forces, the surface having a surface area in an overlapping relationship with the stack;

a second compression means disposed between the first compression means and the stack and comprising a first contact surface area adjacent to the stack and a second contact surface adjacent to the surface, the second contact surface area less than the first contact surface;

a transmission rod having a first end and a second end, the transmission rod adapted to receive ultrasonic vibration form the transducer assembly and to transmit the ultrasonic vibration from the first end to the second end of the transmission rod; and an end effector having a first end and a second end, the end effector adapted to receive the ultrasonic vibration from the transmission rod and to transmit the ultrasonic vibration from the first end to the second end of the end effector.

10. The device of claim 9 further wherein the second compression means comprises at least two contact surfaces adjacent to the surface, wherein the surface area of the at least two contact surfaces is less than the first contact surface area.

11. An ultrasonic device comprising:

a transducer assembly adapted to vibrate at an ultrasonic frequency in response to electrical energy, the transducer assembly comprising a stack of alternating positive and negative electrodes and piezoelectric elements in an alternating relationship with the electrodes and further defining a radial axis r and a longitudinal axis z and further comprising a compression means for applying compression forces to the stack, the compression means comprises a surface for applying compression forces, the surface having a surface area in an overlapping relationship with the stack, and an element having a first contact surface adjacent to the stack and a second contact surface adjacent to the surface, the second contact surface area is less than the first contact surface area; and wherein the stack is subjected in operation to compressive loading resulting in substantially uniform pressure along the r and z axes.

12. The ultrasonic device of claim 11, wherein the element comprises at least two contact surfaces adjacent to the surface, wherein the surface area of the at least two contact surfaces is less than the surface area of the first contact surface.

* * * * *